United States Patent [19]

Pieper

[11] Patent Number: 4,692,281
[45] Date of Patent: Sep. 8, 1987

[54] CARBOXYTETRALINEPHOSPHONIC ACIDS AND PROCESS FOR MAKING THEM

[75] Inventor: Werner Pieper, Kerpen, Fed. Rep. of Germany

[73] Assignee: Hoechst Aktiengesellschaft, Fed. Rep. of Germany

[21] Appl. No.: 859,077

[22] Filed: May 2, 1986

[30] Foreign Application Priority Data

May 18, 1985 [DE]  Fed. Rep. of Germany ....... 3517970

[51] Int. Cl.$^4$ .............................................. C07F 9/38
[52] U.S. Cl. ........................................... 260/502.4 R
[58] Field of Search .................. 260/502.4 P, 502.4 D

[56] References Cited

FOREIGN PATENT DOCUMENTS 2455624  5/1976  Fed. Rep. of Germany ... 260/502.4 P

Primary Examiner—J. E. Evans
Attorney, Agent, or Firm—Connolly and Hutz

[57] ABSTRACT

Novel mono- or dicarboxytetralinephosphonic acids of the general formula I

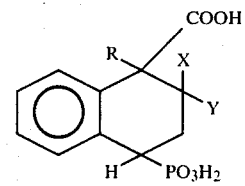

in which
R stands for hydrogen or an alkyl group,
X stands for hydrogen or a carboxylic group, and
Y stands for hydrogen or an alkyl group are made by reacting 1-phenylvinyl-1-phosphonic acid with an unsaturated carboxylic acid of formula II

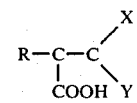

or with its anhydride.

3 Claims, No Drawings

CARBOXYTETRALINEPHOSPHONIC ACIDS AND PROCESS FOR MAKING THEM

The present invention relates to mono- or dicarboxytetralinephosphonic acids of the general formula I

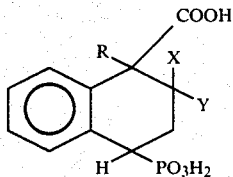

in which
R stands for hydrogen or an alkyl group,
X stands for hydrogen or a carboxylic group, and
Y stands for hydrogen or an alkyl group, not described heretofore, and to a process for making them. The invention relates more particularly to 4-carboxytetraline-1-phosphonic acid and 3,4-dicarboxytetraline-1-phosphonic acid.

1-phenylvinyl-1-phosphonic acid is a compound readily accessible by reacting acetophenone with tetraphosphorus hexoxide (cf. DE-A-31 25 329) or phosphorus trichloride (cf. DE-A-No. 33 23 392).

It is generally accepted that 1-phenylvinyl-1-phosphonic acid can be copolymerized with copolymerizable unsaturated compounds. In Journal of Chromatography 102, 89–94 (1974), for example, reference is made to the production of resins and membranes by subjecting 1-phenylvinyl-1-phosphonic acid to a radical-initiated copolymerization reaction with advinylbenzene, acrylic acid or acrylonitrile.

We have now unexpectedly found that the above novel compounds are obtained by reacting 1-phenylvinyl-1-phosphonic acid with an unsaturated carboxylic acid of the general formula II

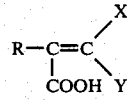

in which
R stands for hydrogen or an alkyl group,
X stands for hydrogen or a carboxylic group and
Y stands for hydrogen or an alkyl group, or with its anhydride, in a quantitative ratio of 1:1–1:4 at a temperature of from 120°–210° C.

Acrylic acid, maleic acid or maleic anhydride are the compounds which are preferably used in the above reaction, which should preferably be carried out at a temperature of from 140°–190° C. over a period of about 1 to 30 hours, depending on the heating temperature selected.

Carboxytetralinephosphonic acids are compounds suitable for use in the after-treatment of phosphatized metal surfaces.

The following Examples illustrate the invention which is naturally not limited thereto.

EXAMPLE 1

30 g 1-phenylvinyl-1-phosphonic acid was heated to 180° C.; next, 11.6 g acrylic acid was added within 1 hour at a rate permitting the reaction temperature to be maintained. After a post-reaction period of 3 hours, the melt obtained (40 g) was taken up in water. $^{31}$P-NMR spectroscopy indicated that the product consisted of two isomeric forms of 4-carboxytetraline-1-phosphonic acid in an isomeric ratio of about 1.3:1.

EXAMPLE 2

184 g 1-phenylvinyl-1-phosphonic acid and 98 g maleic anhydride were heated to 180° C. and stirred at that temperature over a period of 3 hours. The highly viscous product was taken up in 300 ml water. $^{31}$P-NMR-spectroscopy indicated that the product consisted of 3,4-dicarboxytetraline-1-phosphonic acid and minor proportions of 1-phenyltetraline-1,4-diphosphonic acid.

We claim:
1. Mono- and dicarboxytetralinephosphonic acids of the general formula I

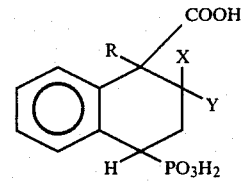

in which R stands for hydrogen or an alkyl group, X stands for hydrogen or a carboxylic group, and Y stands for hydrogen or an alkyl group.
2. 4-carboxytetraline-1-phosphonic acid.
3. 3,4-dicarboxytetraline-1-phosphonic acid.